United States Patent
Lorant (12)

(10) Patent No.: US 6,465,402 B1
(45) Date of Patent: Oct. 15, 2002

(54) COMPOSITION IN THE FORM OF AN OIL-IN-WATER EMULSION AND ITS USES IN PARTICULAR ITS COSMETIC USES

(75) Inventor: Raluca Lorant, Thiais (FR)

(73) Assignee: L'Oreal, Clinchy (FR)

( * ) Notice: Subject to any disclaimer, the term of this patent is extended or adjusted under 35 U.S.C. 154(b) by 0 days.

(21) Appl. No.: 09/579,435

(22) Filed: May 26, 2000

(30) Foreign Application Priority Data

May 26, 1999 (FR) .............................. 99 06659

(51) Int. Cl.⁷ .............................. C11D 3/37; C11D 9/36
(52) U.S. Cl. ...................... 510/136; 510/130; 510/417; 424/70.1; 424/70.12; 514/63
(58) Field of Search ................. 510/417, 130, 510/136; 134/42; 516/204; 424/401, 70.1, 70.12, 449; 514/63

(56) References Cited

U.S. PATENT DOCUMENTS

| | | | |
|---|---|---|---|
| 5,470,551 A | * | 11/1995 | Dubief et al. |
| 5,599,533 A | | 2/1997 | Stepniewski et al. |
| 5,674,509 A | * | 10/1997 | Date et al. |

FOREIGN PATENT DOCUMENTS

| | | |
|---|---|---|
| EP | 0 295 886 | 6/1988 |
| EP | 0 501 791 A2 | 2/1992 |
| EP | 0 706 789 A1 | 8/1995 |
| EP | 0 815 843 A1 | 5/1997 |
| EP | 0 893 467 A2 | 7/1998 |
| JP | 11-021227 | 1/1999 |
| JP | 11-092335 | 6/1999 |

OTHER PUBLICATIONS

U.S. patent application Ser. No. 09/489,842, filed Jan. 24, 2000, pending.
U.S. patent application Ser. No. 09/489,841, filed Jan. 24, 2000, pending.
U.S. patent application Ser. No. 09/579,435, filed May 26, 2000, pending.

* cited by examiner

Primary Examiner—Gregory E. Webb
(74) Attorney, Agent, or Firm—Oblon, Spivak, McClelland, Maier & Neustadt, P.C.

(57) ABSTRACT

The present invention relates to an oil-in-water emulsion composition, including: an oily phase dispersed in an aqueous phase; wherein the oily phase includes at least one crosslinked solid organopolysiloxane elastomer having at least one oxyalkylene group; and wherein the aqueous phase includes at least one polymer which is soluble or swellable in water. The present invention also relates to a cosmetic composition containing the above-noted composition, and methods of using. The present invention makes it possible to prepare oil-in-water emulsions which are stable even though they may not contain a conventionally used surfactant, this stability persisting even when the level of oily phase is high. Furthermore, the present invention provides compositions that are advantageously fresh and comfortable during application to the skin, which effects are otherwise not obtained with conventional compositions.

25 Claims, No Drawings

US 6,465,402 B1

COMPOSITION IN THE FORM OF AN OIL-IN-WATER EMULSION AND ITS USES IN PARTICULAR ITS COSMETIC USES

BACKGROUND OF THE INVENTION

1. Field of the Invention

The present application relates to a composition, and particularly a cosmetic composition, in the form of an oil-in-water emulsion that contains a crosslinked solid organopolysiloxane elastomer having at least one oxyalkylene group and a polymer which is soluble or swellable in water. The application also relates to the use of the composition, particularly in the cosmetics field, and to the use of the combination of the solid organopolysiloxane elastomer and of the polymer which is soluble or swellable in water for the stabilization of an oil-in-water emulsion.

2. Discussion of the Background

For reasons related mostly to comfort of use (softness, emollience and others), current cosmetic compositions are generally provided in the form of an oil-in-water (O/W) emulsion (composed of a continuous aqueous dispersing phase and a non-continuous oily dispersed phase) or a water-in-oil (W/O) emulsion (composed of a continuous oily dispersing phase and a non-continuous aqueous dispersed phase). In the cosmetics field, O/W emulsions are typically more in demand because they include an aqueous phase as the external phase, and the aqueous phase confers upon the composition a fresher, less greasy and lighter feel than W/O emulsions during application to the skin.

The emulsions are generally stabilized by appropriate emulsifying surfactants which, by virtue of their amphiphilic structure, reside at the oil/water interface and thus stabilize the dispersed droplets. These emulsifiers exhibit the disadvantage, however, of penetrating and potentially irritating the skin, eyes and scalp. This is particularly the case for subjects with sensitive skin.

In addition, such emulsions often have inadequate cosmetic and physicochemical properties, e.g., they can have an oily feel and are unstable over time. Increasing the level of surfactants does not generally solve these problems. The required stability is not always achieved, and the cosmetic properties are not improved (the composition exhibits a waxy and heavy feel and a lack of freshness on application). Moreover, as indicated above, it is also inadvisable to use an excessively high level of surfactant, to ensure harmlessness.

One solution for increasing the stability of O/W emulsions (i.e., to reduce creaming and phase separation) is to add thickening agents to the emulsion. The thickening agents create, within the aqueous phase, a gelled matrix. The gelled matrix serves to set the oily droplets and mechanically maintains the entire emulsion. However, it is impossible to obtain with this solution all the desired textures and particularly the light textures which are readily and rapidly applied to the skin without leaving a residual film.

Replacing the surfactants by polymers having, in their chain, a hydrophilic part and a hydrophobic part composed of a fatty chain, such as copolymers of $(C_{10}-C_{30})$alkyl acrylate and of acrylic or methacrylic acid, has been proposed. An example of such a polymer includes the product "Pemulen TR2" sold by Goodrich. However, these polymers undesirably impart a sticky effect when applied to the skin, and it is not possible to obtain a composition which remains stable for a long period of time when the amount of oil is too high.

EP-A-815,844 discloses the use of a crosslinked and neutralized polymer of 2-acrylamido-2-methylpropanesulphonic acid in producing surfactant-free emulsions. However, the emulsions obtained are not completely stable in the presence of a high level of oily phase, for example greater than 12%.

SUMMARY OF THE INVENTION

Accordingly, one object of the invention is to prepare stable oil-in-water emulsions.

Another object of the invention is to prepare stable oil-in-water emulsions that do not exhibit phase separation or release of oil.

Another object of the invention is to prepare stable oil-in-water emulsions that do not depend on emulsifying surfactants conventionally used in O/W emulsions.

Another object of the invention is to prepare stable oil-in-water emulsions that exhibit good cosmetic properties without having the disadvantages of the prior art, whatever the amount of oil present in the emulsion.

These and other objects have been attained with the present invention, the first embodiment of which provides an oil-in-water emulsion composition, including:

an oily phase dispersed in an aqueous phase;

wherein the oily phase includes at least one crosslinked solid organopolysiloxane elastomer having at least one oxyalkylene group; and wherein the aqueous phase includes at least one polymer which is soluble or swellable in water.

Another embodiment of the present invention provides a cosmetic composition, including the above-noted composition according to the invention and a physiologically acceptable medium.

Another embodiment of the present invention provides a method of using the above-noted composition according to the invention for treating, protecting, caring for, removing make-up from and/or cleansing the skin, lips and/or hair and/or for making up the skin and/or lips.

Another embodiment of the present invention provides a process for the cosmetic treatment of the skin, of the hair and/or of the lips, including applying the above-noted composition according to the invention to the skin, hair and/or lips.

Another embodiment of the present invention provides a method of using the above-noted composition according to the invention in the manufacture of a composition for caring for dry skin and/or dry lips.

Another embodiment of the present invention provides a method of stabilizing an oil-in-water emulsion, including preparing an oil-in-water emulsion with at least one a crosslinked solid organopolysiloxane elastomer and at least one polymer which is soluble or swellable in water.

The present invention makes it possible to prepare oil-in-water emulsions which are stable even though they optionally may not contain conventionally used surfactants, this stability persisting even when the level of oily phase is high. Furthermore, the present invention provides compositions that are advantageously fresh and comfortable during application to the skin, which effects are otherwise not obtained with conventional compositions.

DESCRIPTION OF THE PREFERRED EMBODIMENTS

A more complete appreciation of the invention and many of the attendant advantages thereof will be readily obtained as the same becomes better understood by reference to the following detailed description.

Preferably, the invention relates to the use of a combination of a crosslinked solid organopolysiloxane elastomer and of a polymer which is soluble or swellable in water, in particular a crosslinked and neutralized poly(2-acrylamido-2-methylpropanesulphonic acid) polymer. The emulsion obtained is stable, even when it is devoid of an emulsifying surfactant conventionally used in O/W emulsions.

Preferably, the term "physiologically acceptable medium" is understood to mean, in the composition of the invention, a nontoxic medium capable of being applied to the skin (including the inside of the eyelids), the lips, the nails or the hair of human beings.

Preferably, the term "solid elastomer" is understood to mean a flexible and deformable material having viscoelastic properties and in particular the consistency of a sponge or of a flexible sphere. Its modulus of elasticity is such that this material is resistant to deformation and has a limited ability to expand and to contract. This material is capable of returning to its original shape after it has been stretched. This elastomer is formed of polymeric chains of high molecular weight, the mobility of which is limited by a uniform network of crosslinking points.

Preferably, the oily phase contains at least one crosslinked solid organopolysiloxane elastomer having at least one oxyalkylene group, and the aqueous phase contains at least one polymer that is swellable or soluble in water.

The oxyalkylenated organopolysiloxane elastomers used in the composition of the invention are known for allowing the preparation of a W/O emulsion and it is entirely unexpected that it should be possible to use them, in combination with a polymer which is soluble or swellable in water, to stabilize an O/W emulsion including a high level of oily phase.

Preferably, the organopolysiloxanes of the composition of the invention include one or more oxyalkylene and in particular oxyethylene (OE) groups, for example from 1 to 40 oxyalkylene units, preferably 1 to 20 and better still 10 to 20 oxyalkylene units, which can form polyoxyalkylene and in particular polyoxyethylene chains. These groups can be pendant, at the chain end or intended to connect two parts of the silicone structure. The silicon atoms carrying these groups preferably number from approximately 1 to 10 and better still from 1 to 6.

Although the invention preferably relates to organopolysiloxanes that contain oxyethylene groups(s) (most preferably including only oxyethylene groups as oxyalkylene groups), it can also relate to organopolysiloxanes that contain oxypropylene group(s), that is to say most preferably including only oxypropylene groups as oxyalkylene groups. The organopolysiloxanes can also include both one or more oxyethylene (OE) group(s), for example 1 to 20, more preferably 2–10; and one or more oxypropylene (OP) group (s), for example 0 to 20, more preferably 1–20, and most preferably 10–20; these organopolysiloxanes are also known as organopolysiloxanes including alkylethoxy-propylene group(s). The number of oxyethylene groups is preferably greater than the number of oxypropylene groups.

The silicone structure forming the polymeric backbone of the organopolysiloxane including oxyalkylene group(s) is preferably a polydimethylsiloxane (PDMS) structure, a portion of the methyl groups of which is optionally substituted by $C_2$ to $C_{30}$ and preferably $C_8$ to $C_{24}$ and better still from $C_{10}$ to $C_{20}$ alkyl groups or phenyl groups, either at the chain end or at pendant positions.

The organopolysiloxane that contains oxyalkylene group (s) can preferably include one or more silicone backbone(s) connected to one another by one or more oxyalkylene and more preferably oxyethylene groups as defined above or by one or more alkylene groups, the alkylene group number ranging from 1 to 20 and preferably from 1 to 10. It preferably includes at least two polymeric backbones connected to one another. The silicone backbone or backbones of the organo-polysiloxanes of the composition according to the invention preferably include from 26 to 80 silicon atoms.

The organopolysiloxane elastomers of the composition of the invention do not dry out the skin and exhibit good cosmetic properties such as softness, freshness and mattness. These elastomers result in compositions which are comfortable on application, spread well, are soft and are not sticky to the touch. These cosmetic properties are believed to be due, on the one hand, to the texture of the organopolysiloxanes and, on the other hand, to their properties, comparable to those of microsponges, of trapping oily media and in particular those of the composition and those secreted by the skin.

The organopolysiloxane elastomers used in the composition in accordance with the invention are partially or completely crosslinked and have a three-dimensional structure. When included in an oily phase, they are converted, according to the level of oily phase used, from a product with a spongy appearance, when they are used in the presence of small contents of oily phase, to a homogeneous gel, in the presence of larger amounts of oily phase. The gelling of the oily phase by these elastomers can be complete or partial.

The organopolysiloxane elastomers used according to the invention can be provided in the form of a powder or gel including an organopolysiloxane elastomer with a three-dimensional structure dispersed in an oily phase. This oily phase, also known as liquid fatty phase, can include any non-aqueous substance or mixture of non-aqueous substances which is liquid at room temperature (approximately 25° C.) and at atmospheric pressure (760 mm of Hg).

The organopolysiloxane elastomers used according to the invention can be preferably chosen from the crosslinked polymers obtained by an addition and crosslinking reaction in a non-aqueous medium, in the presence of a catalyst, preferably of the platinum type (i.e., of the platinum group as it is typically known in the art), of at least:

(a) one first organopolysiloxane (i) having at least two vinyl groups in the α,ω-position of the silicone chain; and (b) one second organopolysiloxane (ii) having at least one hydrogen atom bonded to a silicon atom per molecule and at least one oxyalkylene, in particular oxyethylene, group.

The organopolysiloxane (i) is preferably chosen from polydimethylsiloxanes (PDMSs) and is more preferably an α,ω-dimethylvinylpolydimethylsiloxane. The organopolysiloxane (ii) is preferably chosen from polydimethylsiloxanes including one or more hydrogen atom(s), each bonded to a silicon atom, and one or more oxyethylene groups and optionally one or more oxypropylene groups bonded to a silicon atom via an alkylene radical having from 1 to 22 carbon atoms.

The silicone chains of the first and second organopolysiloxanes (i) and (ii) each independently optionally include $C_1$ to $C_6$ alkyl pendant chains and/or aryl chains.

The organopolysiloxane elastomers of the composition according to the invention are preferably provided in an oily phase, with which they constitute an anhydrous gel. This gel can preferably be obtained as follows:

(a) mixing the first organopolysiloxane (i) and the second organopolysiloxane (ii);

(b) adding the oily phase to the mixture of stage (a); and
(c) polymerizing the first organopolysiloxane (i) and the second organopolysiloxane (ii) in the oily phase in the presence of a platinum catalyst.

The oily phase used during the manufacture of the anhydrous gel preferably includes one or more oils which are liquid at room temperature (25° C.) chosen from hydrocarbonaceous oils and/or silicone oils. The oily phase is preferably a silicone liquid phase preferably including one or more oils chosen from polydimethylsiloxanes (PDMSs) with a linear or cyclic chain which are liquid at room temperature, optionally including a pendant alkyl or aryl chain or an alkyl or aryl chain at the chain end, the alkyl chain having from 1 to 6 carbon atoms.

The organopolysiloxanes of the invention are preferably obtained according to the procedure of Examples 3, 4 and 8 of U.S. Pat. No. 5,412,004 and of the examples of U.S. Pat. No. 5,811,487, the entire contents of each of which are hereby incorporated by reference.

According to a preferred embodiment of the invention, use is made, as organopolysiloxanes, of that sold under the reference KSG 21 by the company Shin Etsu or the product of Example 3 (synthetic example) of U.S. Pat. No. 5,412,004.

KSG 21 is provided in the form of a pasty gel including approximately 28% of organopolysiloxane and 72% of silicone oil (PDMS) having a viscosity of 6 cSt (i.e., $6 \times 10^{-6}$ m$^2$/s).

The product of Example 3 of U.S. Pat. No. 5,412,004 is provided in the form of a pasty gel including approximately 33% by weight of crosslinked organopolysiloxane including oxyethylene group(s) and approximately 67% of 6 cSt PDMS (i.e., $6 \times 10^{-6}$ m$^2$/s). The organopolysiloxane includes approximately 18% of ethylene oxide by weight with respect to the total weight of the polymer.

Preferably, the organopolysiloxane elastomer pasty gel used in the composition of the invention has a plastic rheological behaviour exhibiting a viscosity, at low shear in the region of $10^{-3}$ s$^{-1}$ or $10^{-4}$ s$^{-1}$, ranging from $2 \times 10^6$ poises to $4 \times 10^6$ poises ($2 \times 10^5$ Pa.s to $4 \times 10^5$ Pa.s) and a dynamic viscosity of 15 to 50 poises (1.5 to 5 Pa.s) for a shear rate of 200 s$^{-1}$ at $t_{10\ minutes}$, measured with an RS 75 (Haake) controlled-stress rheometer at 25° C. in cone/plate geometry; characteristics of the cone: diameter of 20 mm, angle of 1° and gap of 40 $\mu$m. This organopolysiloxane preferably has a viscoelastic behaviour with a dominant elastic nature at low values of the shear stress defined as follows: 800 Pa<$G^*_{plate}$<2500 Pa with $\delta_{plate}$ in the region of 10°, $G^*_{plate}$ representing the rigidity modulus (or complex modulus), that is to say the consistency, and being measured at 1 Hz and $\delta_{plate}$ representing the elasticity (or loss angle). It exhibits a flash point of approximately 170° C. at atmospheric pressure.

For the product of Example 3 (synthetic example) of U.S. Pat. No. 5,412,004, the dynamic viscosity, under the conditions indicated above, is 45 poises (4.5 Pa.s).

The organopolysiloxane elastomer is preferably introduced into the oily phase of the emulsion according to the invention.

The organopolysiloxane elastomer gel used in the composition of the invention is preferably present in the composition at a content ranging from approximately 0.03 to 40% and preferably from 1.5 to 20% by weight with respect to the total weight of the composition, which corresponds to a level of organopolysiloxane elastomer, as active material, ranging approximately from 0.01 to 10% by weight and better still from 0.5 to 5% by weight with respect to the total weight of the composition.

Preferably, the particles of organopolysiloxane elastomer (as active material) have a size ranging from 0.1 to 500 $\mu$m, preferably from 3 to 200 $\mu$m and better still from 3 to 50 $\mu$m. These particles can be spherical, flat or amorphous with preferably a spherical shape.

Preferably, the polymers which are soluble or swellable in water which are used in the composition of the invention are gelling agents, and they can be preferably chosen from carboxyvinyl polymers; acrylic or methacrylic copolymers; natural gums; polysaccharides; acrylamide polymers and copolymers; vinyl ether copolymers; or cationic polymers, such as polyquaternium. Use may also be made of a mixture of these polymers.

Preferable carboxyvinyl polymers include, for example, crosslinked polymers of acrylic acid, such as the products sold under the names Carbopols 980, 981, 954, 2984 and 5984 (CTFA name: carbomer) by the company Goodrich or the products sold under the names Synthalen M and Synthalen K by the company 3 VSA.

Homopolymers of dimethylaminoethyl methacrylate which is quaternized by methyl chloride, such as the products sold under the names Salcare 95 and Salcare 96 by the company Allied Colloids, are preferable.

Preferable acrylic or methacrylic copolymers include the copolymers of $C_{10}$–$C_{30}$ alkyl acrylates and of acrylic or methacrylic acid or of their esters which are sold under the names Pemulen TR1, Pemulen TR2 or Carbopol 1342 by the company Goodrich (CTFA name: Acrylates/C10–30 Alkyl Acrylate Crosspolymer).

Copolymers of dimethylaminoethyl methacrylate, which is quaternized by methyl chloride, and of acrylamide, such as the product Salcare SC92 sold by Allied Colloids or the product PAS 5194 sold by Hoechst, and crosslinked copolymers of vinyl isodecanoate and of acrylic and methacrylic acid, such as the product Stabylen 30 sold by the company 3M, are preferable.

Natural gums, of, for example, xanthan gum, gellan gum or locust bean gum, are preferable.

Polysaccharides, of cellulose derivatives, such as, for example, hydroxypropylmethylcellulose or carboxymethylcellulose, are preferable.

Preferable acrylamide copolymers include the crosslinked copolymer of acrylamide and of 2-acrylamido-2-methylpropanesulphonic acid, in particular the mixture sold under the name Sepigel 305 by the Company Seppic which is provided in the form of an emulsion including approximately 40% of copolymer (CTFA name: polyacrylamide/C13–14 isoparaffin/laureth-7).

Preferable vinyl ether copolymers include, for example, crosslinked PVM/MA decadiene copolymers, such as Stabileze 06 sold by the company ISP.

Preferable acrylamide polymers include crosslinked and virtually or completely neutralized poly(2-acrylamido-2-methylpropanesulphonic acid) polymers, characterized in that they preferably include, distributed randomly:

a) from 90 to 99.9% by weight of units of following general formula (I):

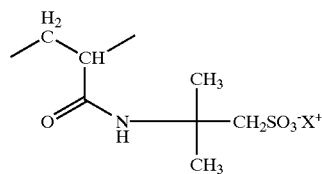

in which $X^+$ denotes a cation or a mixture of cations, it being preferable for at most 10 mol % of the $X^+$ cations to be $H^+$ protons;

b) from 0.01 to 10% by weight of crosslinking units originating from at least one monomer having at least two olefinic double bonds; the proportions by weight being defined with respect to the total weight of the polymer.

These poly(2-acrylamido-2-methylpropanesulphonic acid) polymers preferably include a number of units of formula (I) in an amount sufficiently high to produce polymer particles with a hydrodynamic volume in solution in water exhibiting a radius ranging from 10 to 500 nm and with a homogeneous and unimodal distribution.

In the formula (I), $X^+$ represents a cation or a mixture of cations chosen in particular from a proton, an alkali metal cation, a cation equivalent to that of an alkaline earth metal or the ammonium ion.

More preferably, 90 to 100 mol % of the cations are $NH_4^+$ cations and 0 to 10 mol % are protons ($H^+$).

According to a preferred embodiment of the invention, use is made, as polymers which are soluble or swellable in water, of poly(2-acrylamido-2-methylpropanesulphonic acid) polymers including from 98 to 99.5% by weight of units of formula (I) and from 0.2 to 2% by weight of crosslinking units.

The crosslinking monomers having at least two olefinic double bonds are preferably chosen, for example, from dipropylene glycol diallyl ether, polyglycol diallyl ethers, triethylene glycol divinyl ether, hydroquinone diallyl ether, tetraallyloxyethane or other allyl or vinyl ethers of polyfunctional alcohols, tetraethylene glycol diacrylate, triallylamine, trimethylolpropane diallyl ether, methylenebisacrylamide or divinylbenzene.

The crosslinking monomers having at least two olefinic double bonds are chosen more preferably from those corresponding to the following general formula (II):

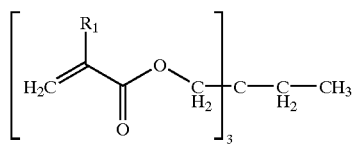

(II)

in which $R_1$ denotes a hydrogen atom or a $C_1$–$C_4$ alkyl and more particularly methyl. The crosslinking monomer is preferably trimethylolpropane triacrylate (compound of formula II where $R_1$ is hydrogen).

The crosslinking reaction of the poly(2-acrylamido-2-methylpropanesulphonic acid) polymers used in the invention produces not only linear chains but also branched or crosslinked polymer molecules. These molecules can be characterized in particular by their Theological behaviour in water but more particularly by dynamic light scattering. In the case of the characterization of molecules by dynamic light scattering, the distribution of the hydrodynamic volume of the structures of the polymer is measured. Macromolecules dissolved in water are flexible and surrounded by a solvation envelope formed from water molecules. With charged polymers, such as those preferably within the invention, the size of the molecules preferably depends on the amount of salt in the water. In polar solvents, the uniform charge along the main chain of the polymer results in a significant expansion in the polymer chain. Increasing the amount of salt increases the amount of electrolyte in the solvent and screens the uniform charges of the polymer. In addition to the molecules transported in the solvation envelope, solvent molecules are fixed in the cavities of the polymer. In this case, the solvent molecules form part of the dissolved macromolecules and move at the same average speed. Thus, the hydrodynamic volume preferably describes the linear dimension of the macromolecule and of these solvation molecules.

The hydrodynamic volume $v_h$ is determined by the following formula:

$$v_h = M/N_A \times (V_2 + dV_1)$$

with:
M denoting the mass in grams of the undissolved macromolecule;
$N_A$ denoting Avogadro's number;
$V_1$ denoting the specific volume of the solvent;
$V_2$ denoting the specific volume of the macromolecule;
d denoting the mass in grams of the solvent which is associated with 1 gram of undissolved macromolecule.

If the hydrodynamic particle is spherical, it is then easy to calculate the hydrodynamic radius from the hydrodynamic volume by the formula:

$$v_h = 4\Pi R^3/3$$

with R denoting the hydrodynamic radius.

Cases where the hydrodynamic particles are perfect spheres are believed to be extremely rare. Preferably, the majority of synthetic polymers involve compacted structures or ellipsoids of high eccentricity. In this case, the radius is determined with respect to a sphere which is equivalent from a frictional viewpoint to the shape of the particle under consideration.

As a general rule, the determination is carried out with respect to molecular weight distributions and thus with respect to hydrodynamic radius and volume distributions. For polydispersed systems, the distribution of the scattering coefficients must be calculated. From this distribution, the results relating to the radial distribution and to the distribution of the hydrodynamic volumes are deduced therefrom.

The hydrodynamic volumes of the poly(2-acrylamido-2-methylpropanesulphonic acid) polymers of the invention are preferably determined by dynamic light scattering from the Stokes-Einstein diffusion coefficients D of formula: $D = kT/6\Pi\eta R$ where k is Boltzmann's constant, T is the absolute temperature in degrees Kelvin, $\eta$ is the viscosity of the solvent (water) and R is the hydrodynamic radius.

These diffusion coefficients D are measured according to the method of characterization of a mixture of polymers by laser scattering described in the following references, the entire contents of each of which are hereby incorporated by reference:

(1) Pecora, R; Dynamic Light Scattering; Plenium Press, New York, 1976;
(2) Chu B; Dynamic Light Scattering; Academic Press, New York, 1994;
(3) Schmitz, K S; Introduction to Dynamic Light Scattering; Academic Press, New York, 1990;
(4) Provincher S. W.; Comp. Phys., 27, 213, 1982;
(5) Provincher S. W.; Comp. Phys., 27, 229, 1982;
(6) ALV Laservertriebgesellschaft mbH, Robert Bosch Str. 47, D-63225 Langen, Germany;
(7) ELS-Reinheimer Strasse 11, D-64846 Gross-Zimmern, Germany;
(8) Chi Wu et al., Macromolecules, 1995, 28, 4914–4919.

The particularly preferred poly(2-acrylamido-2-methylpropanesulphonic acid) polymers are those exhibiting a viscosity, measured with a Brookfield viscometer, rotor 4, at a rotational speed of 100 revolutions/minute in a 2% aqueous solution at a temperature of approximately 25° C., of greater than or equal to 1000 cPs (or 1000 mPa.s) and more preferably ranging from 5000 to 40,000 cPs (5000 to 40,000 mPa.s) and more particularly from 6500 to 35,000 cPs (6500 to 35,000 mPa.s).

Preferably, the crosslinked poly(2-acrylamido-2-methylpropanesulphonic acid)s used in the composition of the invention can be obtained according to the preparation process including the following stages:

(a) the 2-acrylamido-2-methylpropanesulphonic acid monomer is dispersed or dissolved in the free form in a tert-butanol or water and tert-butanol solution;

(b) the solution or the dispersion of monomer obtained in (a) is neutralized with one or a number of inorganic or organic bases, preferably ammonia $NH_3$, in an amount which makes it possible to obtain a degree of neutralization of the sulphonic acid functional groups of the polymer ranging from 90 to 100%;

(c) the crosslinking monomer or monomers is/are added to the solution or dispersion obtained in (b);

(d) a conventional radical polymerization is carried out in the presence of free radical initiators at a temperature ranging from 10 to 150° C., the polymer precipitating in the solution or dispersion based on tert-butanol.

Preferably, the crosslinked poly(2-acrylamido-2-methylpropanesulphonic acid) used in the composition of the invention can be the product sold by the company Hoechst under the trade name "Hostacerin AMPS" (CTFA name: ammonium polyacryldimethyltauramide).

The polymer which is soluble or swellable in water used in the composition of the invention is preferably introduced into the aqueous phase of the emulsion according to the invention.

The polymer which is soluble or swellable in water used in the composition of the invention is preferably present in an amount, as active material, ranging from 0.1 to 10% by weight, better still from 0.2 to 5% by weight and more preferably from 0.5 to 2% by weight with respect to the total weight of the composition.

In addition to the oils optionally present in the organopolysiloxane elastomer gel, the oily phase can be of any nature and can include oils, waxes or gums which are solid at room temperature or pasty fatty substances of animal, vegetable, mineral or synthetic origin and their mixtures. The oils can be volatile at room temperature and at atmospheric pressure. Preferably, the term "volatile oil" is understood to mean in particular an oil capable of evaporating, in less than one hour, on contact with the skin or lips which has in particular a non-zero vapour pressure, especially ranging from $10^{-3}$ to 300 mm of Hg (at room temperature and atmospheric pressure) and preferably greater than 0.3 mm of Hg.

Preferable oils which can be used in the composition of the invention include:

hydrocarbonaceous oils of animal origin, such as perhydrosqualene;

hydrocarbonaceous oils of vegetable origin, such as liquid fatty acid triglycerides, for example sunflower, maize, soybean, cucumber, grape seed, sesame, hazelnut, apricot, macadamia, castor or avocado oils, or triglycerides of caprylic/capric acids, such as those sold by the company Stearineries Dubois or those sold under the names Miglyol 810, 812 and 818 by the company Dynamit Nobel;

oils of formula $R^1COOR^2$, in which $R^1$ represents the residue of a higher fatty acid including from 7 to 19 carbon atoms and $R^2$ represents a branched hydrocarbonaceous chain including from 3 to 20 carbon atoms, such as, for example, purcellin oil, isopropyl myristate, or octanoates, decanoates or ricinoleates of alcohols or of polyalcohols;

linear or branched hydrocarbons of mineral or synthetic origin, such as volatile or non-volatile liquid paraffins and their derivatives, liquid petrolatum, polydecenes or hydrogenated polyisobutene, such as parleam;

synthetic ethers of formula $R^3OR^4$, in which $R^3$ is a $C_3$ to $C_{19}$ alkyl radical and $R^4$ is a $C_3$ to $C_{20}$ alkyl radical;

fatty alcohols, such as octyldodecanol or oleyl alcohol;

fluorinated oils which are partially hydrocarbonaceous and/or silicone-containing, such as perfluoropolyesters;

silicone oils, such as polymethylsiloxanes with a linear or cyclic silicone chain which are liquid or pasty at room temperature, phenyl dimethicones, phenyl trimethicones, polymethylphenylsiloxanes, or alkylpolydimethylsiloxanes with a $C_2$ to $C_{20}$ alkyl chain;

and mixtures thereof.

Preferably, the amount of oily phase in the composition of the invention can range from 1 to 50% by weight, more preferably from 5 to 40% and better still from 7 to 30% by weight with respect to the total weight of the composition.

The emulsion of the invention is preferably devoid of surfactant conventionally used in O/W emulsions and it exhibits, for this reason, the advantage of not being irritating to particularly sensitive skin. In addition, this emulsion exhibits the advantage of making possible the incorporation of heat-sensitive active principles because it can be manufactured at room temperature.

The compositions of the invention can preferably include conventional adjuvants known to those of ordinary skill in this art, such as hydrophilic or lipophilic active principles, conventional gelling and/or thickening agents, preservatives, antioxidants, solvents, fillers, colouring materials, basic or acidic agents and lipid vesicles. Preferably, these adjuvants are used in the proportions usual in the cosmetics field, for example, from 0.01 to 30% of the total weight of the emulsion, and they are, depending on their nature, introduced into the aqueous phase or into the oily phase of the emulsion or alternatively into vesicles. These adjuvants and their concentrations must be such that they do not modify the property desired for the emulsion of the invention.

Preferable solvents include, for example, linear or branched monoalcohols having from 1 to 8 carbon atoms, such as ethanol, propanol, butanol, isopropanol or isobutanol; poly(ethylene glycol)s having from 6 to 80 ethylene oxides; or polyols, such as propylene glycol, isoprene glycol and butylene glycol.

Preferable active principles include, for example, moisturizing agents such as polyols, for example glycerol and sorbitol; keratolytic agents, such as α-hydroxy acids; salicylic acid and its derivatives; vitamins, such as vitamin C, vitamin A and vitamin E and their derivatives, in particular their esters; depigmenting agents; slimming agents; screening agents; and any active principle appropriate for the final purpose of the composition.

Preferably, the composition of the invention can be used in topical application, in particular in the cosmetics and dermatological fields. This composition can be more or less fluid and have the appearance of a white or coloured cream, of an ointment, of a milk, of a lotion, of a serum, of a paste or of a foam. The composition of the invention can be applied topically to the face, including around the eyes, to the body and to the scalp of human beings.

The composition according to the invention is particularly suitable in a large number of cosmetic treatments of the skin, of the lips and of the hair, including the scalp, in particular for treating, protecting, caring for, removing make-up from and/or cleansing the skin, lips and/or hair and/or for making up the skin and/or lips. It is also suitable for treating dry skin and/or dry lips.

The composition according to the invention can preferably be used as a care, make-up removing and/or cleansing product for the face in the form of a cream or milk, as a make-up product (skin and lips), by incorporation of fillers or of colorants, or as antisun products, by incorporation of screening agents.

A preferred embodiment of the invention is an oil-in-water emulsion composition, wherein the oily phase contains at least one crosslinked solid organopolysiloxane elastomer having at least one oxyalkylene group, and the aqueous phase contains at least one polymer that is swellable or soluble in water.

Another preferred embodiment of the invention provides a composition in the form of an oil-in-water emulsion including an oily phase dispersed in an aqueous phase, characterized in that it includes, in a physiologically acceptable medium, (1) at least one crosslinked solid organopolysiloxane elastomer including at least one oxyalkylene group and (2) at least one polymer which is soluble or swellable in water.

A preferable embodiment of the invention is consequently the cosmetic use of the composition as defined above for treating, protecting, caring for, removing make-up from and/or cleansing the skin, lips and/or hair and/or for making up the skin and/or lips.

Another preferable embodiment of the invention is a process for the cosmetic treatment of the skin, including the scalp, of the hair and/or of the lips, characterized in that a composition as defined above is applied to the skin, hair and/or lips.

Another preferable embodiment of the invention is the use of the composition as defined above in the manufacture of a composition intended for caring for dry skin and/or dry lips.

EXAMPLES

Having generally described this invention, a further understanding can be obtained by reference to certain specific examples, which are provided herein for purposes of illustration only and are not intended to be limiting unless otherwise specified. The amounts shown are as % by weight, unless otherwise mentioned.

Example 1

Care Cream

| Aqueous phase: | |
| --- | --- |
| Hostacerin AMPS (sold by the company Hoechst) | 2% |
| Preservatives | 0.4% |
| Demineralized water | q.s. for 100% |
| Oily phase: | |
| Hydrogenated isobutene | 10% |
| Volatile silicone oil | 10% |
| KSG 21 (containing 28% of active material) (i.e. 0.84% of active material) | 3% |

Procedure: The aqueous phase is prepared by dispersing, with stirring, the Hostacerin AMPS in the water containing the preservatives and the glycerol. The KSG 21 is then dispersed in the liquid oily phase and emulsification is subsequently carried out by dispersing, with vigorous stirring, the mixture obtained in the aqueous phase.

A stable and slightly translucent cream is obtained which is very soft and fresh on the skin. The cream is fine and even under the microscope.

Comparative Example

A composition identical to that of Example 1 but not including KSG21 is prepared. An unstable emulsion is obtained which proves to be uneven and coarse under the microscope Example 2

Care Cream

| Aqueous phase: | |
| --- | --- |
| Sepigel 305 (sold by the company Seppic) | 2% |
| Preservatives | 0.4% |
| Glycerol | 3% |
| Demineralized water | q.s. for 100% |
| Oily phase: | |
| Volatile silicone oil (cyclohexasiloxane) | 7% |
| Apricot oil | 5% |
| KSG 21 (containing 28% of active material) (i.e. 1.4% of active material) | 5% |

Procedure: The aqueous phase is prepared by dispersing, with stirring, the Sepigel 305 in the water containing the preservatives and the glycerol. The KSG 21 is then dispersed in the liquid oily phase and emulsification is subsequently carried out by dispersing, with vigorous stirring, the mixture obtained in the aqueous phase.

A slightly translucent cream is obtained which is very soft and fresh on the skin.

Example 3

Mattifying Foundation

| Aqueous phase: | |
| --- | --- |
| Hostacerin AMPS (sold by the company Hoechst) | 1.2% |
| Preservatives | 0.4% |
| Glycerol | 3% |
| Demineralized water | q.s. for 100% |
| Oily phase: | |
| Volatile silicone oil (cyclohexasiloxane) | 10% |
| KSG 21 (containing 28% of active material) (i.e. 0.84% of active material) | 3% |
| Colouring phase: | |
| Titanium oxide | 4% |
| Iron oxides | 0.8% |

Procedure: The aqueous phase is prepared by dispersing, with stirring, the Hostacerin AMPS in the water containing the preservatives and the glycerol. The colouring phase and then the KSG 21 are dispersed in the liquid oily phase and emulsification is subsequently carried out by dispersing, with vigorous stirring, the mixture obtained in the aqueous phase.

A tinted cream is obtained which is nongreasy and soft.

Example 4
Antisun Care

| Aqueous phase: | |
|---|---|
| Hostacerin AMPS (sold by the company Hoechst) | 2% |
| Preservatives | 0.4% |
| Glycerol | 3% |
| Demineralized water | q.s. for 100% |
| Oily phase: | |
| Volatile silicone oil (cyclohexasiloxane) | 5% |
| Octyl methoxycinnamate (screening agent) | 7% |
| Organopolysiloxane elastomer gel (Example 3 of U.S. Pat. No. 5,412,004 containing 33% of active material) (i.e. 1.32% of active material) | 4% |

Procedure: The aqueous phase is prepared by dispersing, with stirring, the Hostacerin AMPS in the water containing the preservatives and the glycerol. The organopolysiloxane gel is dispersed in the liquid oily phase and emulsification is subsequently carried out by dispersing, with vigorous stirring, the mixture obtained in the aqueous phase.

A soft, light cream is obtained.

Example 5
Make-up Removing Composition for Sensitive Skin

| Aqueous phase: | |
|---|---|
| Hostacerin AMPS (sold by the company Hoechst) | 1.5% |
| Preservatives | 0.4% |
| Glycerol | 3% |
| Demineralized water | q.s. for 100% |
| Oily phase: | |
| Volatile silicone oil (cyclohexasiloxane) | 5% |
| Octyl palmitate | 5% |
| Organopolysiloxane gel (Example 3 of Patent U.S. Pat. No. 5,412,004) (i.e. 66% of active material) | 2% |

Procedure: The aqueous phase is prepared by dispersing, with stirring, the Hostacerin AMPS in the water containing the preservatives and the glycerol. The organopolysiloxane gel is then dispersed in the liquid oily phase and emulsification is subsequently carried out by dispersing, with vigorous stirring, the mixture obtained in the aqueous phase.

A rich emulsion is obtained which removes make-up gently from delicate skin.

Example 6
Care Composition

| Aqueous phase: | |
|---|---|
| Sepigel 305 (sold by the company Seppic) | 2% |
| Preservatives | 0.4% |
| Glycerol | 5% |
| Demineralized water | q.s. for 100% |
| Oily phase: | |
| Volatile silicone oil (cyclopentasiloxane) | 10% |
| Hydrogenated isobutene | 10% |
| Organopolysiloxane gel (Example 3 of Patent U.S. Pat. No. 5,412,004) (i.e. 0.66% of active material) | 2% |

The preparation process includes dispersing, with stirring, the Sepigel in the water containing the preservatives and the glycerol. The organopolysiloxane gel is then dispersed in the liquid oily phase and emulsification is subsequently carried out by dispersing, with vigorous stirring, the mixture obtained in the aqueous phase.

A cream is obtained which is soft and very pleasant during application to the skin, which it leaves supple and matt.

Obviously, numerous modifications and variations of the present invention are possible in light of the above teachings. It is therefore to be understood that within the scope of the appended claims, the invention may be practiced otherwise than as specifically described herein.

This application is based on French application FR 99 06659, filed May 26, 1999, the entire contents of which are hereby incorporated by reference.

What is claimed is:

1. An oil-in-water emulsion composition, comprising:
   an oily phase dispersed in an aqueous phase;
   wherein the oily phase comprises at least one crosslinked solid organopolysiloxane elastomer comprising at least one oxyalkylene group; and
   wherein the aqueous phase comprises at least one polymer which is soluble or swellable in water.

2. The composition according to claim 1, wherein said composition is devoid of surfactant.

3. The composition according to claim 1, wherein said organopolysiloxane elastomer comprises at least one oxyethylene group.

4. The composition according to claim 1, wherein said oxyalkylene group consists of one or more oxyethylene group.

5. The composition according to claim 1, wherein said organopolysiloxane elastomer is obtained by an addition and crosslinking reaction in a non-aqueous medium, in the presence of a catalyst, of at least:
   one first organopolysiloxane (i) having two vinyl groups in the $\alpha,\omega$-position of the silicone chain per molecule; and
   one second organopolysiloxane (ii) having at least one hydrogen atom bonded to a silicon atom per molecule and at least one oxyalkylene group.

6. The composition according to claim 5, wherein said first organopolysiloxane (i) is a polydimethylsiloxane.

7. The composition according to claim 5, wherein said first organopolysiloxane (i) is an $\alpha,\omega$-dimethylvinylpolydimethylsiloxane.

8. The composition according to claim 5, wherein said second organopolysiloxane (ii) is selected from the group consisting of polydimethylsiloxanes having one or more hydrogen atoms and one or more oxyalkylene groups bonded to a silicon atom via an alkylene radical having from 1 to 22 carbon atoms.

9. The composition according to claim 1, wherein said organopolysiloxane is in the form of a gel obtained according to a process, comprising:
   (a) mixing first and second organopolysiloxanes (i) and (ii) to form a mixture, said first organopolysiloxane (i) having two vinyl groups in the $\alpha\omega$-position of the silicone chain per molecule, and said second organopolysiloxane (ii) having at least one hydrogen atom bonded to a silicon atom per molecule and at least one oxyalkylene group;
   (b) adding an oily phase to the mixture of stage (a);
   (c) polymerizing said first and second organopolysiloxanes (i) and (ii) in the oily phase in the presence of a platinum catalyst.

10. The composition according to claim 1, wherein said organopolysiloxane is in the form of a gel, said gel having a rigidity modulus $G^*_{plate}$, measured at 1 Hz, defined as follows: 800 Pa<$G^*_{plate}$<2500 Pa with $\delta_{plate}$ in the region of 10°, $\delta_{plate}$ representing the elasticity.

11. The composition according to claim 1, wherein said organopolysiloxane elastomer represents from 0.01 to 10% of active material by weight with respect to the total weight of the composition.

12. The composition according to claim 1, wherein said polymer which is soluble or swellable in water is selected from the group consisting of carboxyvinyl polymers; acrylic or methacrylic copolymers; natural gums; polysaccharides; acrylamide polymers and copolymers; vinyl ether copolymers; cationic polymers; and mixtures thereof.

13. The composition according to claim 1, wherein said polymer which is soluble or swellable in water is a crosslinked poly(2-acrylamido-2-methylpropanesulphonic acid) neutralized to at least 90% comprising, distributed randomly:
(a) from 90 to 99.9% by weight of units having the following formula (I):

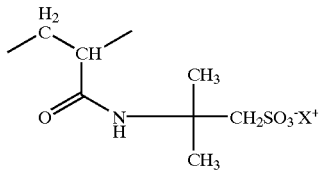

in which X⁺ denotes a cation or a mixture of cations, wherein at most 10 mol % of the X⁺ cations are H⁺ protons;
(b) from 0.01 to 10% by weight of crosslinking units originating from at least one monomer having at least two olefinic double bonds; the proportions by weight being defined with respect to the total weight of the polymer.

14. The composition according to claim 13, wherein said poly(2-acrylamido-2-methylpropanesulphonic acid) comprises from 98 to 99.5% by weight of units of formula (I) and from 0.2 to 2% by weight of crosslinking units.

15. The composition according to claim 13, wherein the X⁺ cation is NH₄⁺.

16. The composition according to claim 13, wherein said crosslinking units comprise monomers having the following formula (II):

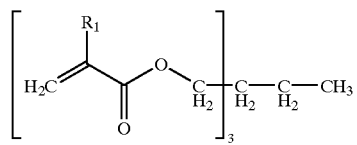

in which $R_1$ denotes hydrogen or a $C_1$–$C_4$ alkyl.

17. The composition according to claim 13, wherein said poly(2-acrylamido-2-methylpropanesulphonic acid) is crosslinked by trimethylolpropane triacrylate.

18. The composition according to claim 1, wherein the amount of said polymer which is soluble or swellable in water ranges from 0.1 to 10% by weight of active material with respect to the total weight of the composition.

19. The composition according to claim 1, wherein said oily phase further comprises at least one selected from the group consisting of oils, waxes, gums, pasty fatty substances and mixtures thereof.

20. The composition according to claim 1, wherein the amount of oily phase ranges from 1 to 50% by weight with respect to the total weight of the composition.

21. A cosmetic composition, comprising the composition according to claim 1 and a physiologically acceptable medium.

22. A method of using the composition according to claim 1 for treating, protecting, caring for, removing make-up from and/or cleansing the skin, lips and/or hair and/or for making up the skin and/or lips.

23. A process for the cosmetic treatment of the skin, of the hair and/or of the lips, comprising applying the composition according to claim 1 to the skin, hair and/or lips.

24. A method of using the composition according to claim 1 in the manufacture of a composition for caring for dry skin and/or dry lips.

25. A method of stabilizing an oil-in-water emulsion, comprising preparing an oil-in-water emulsion with at least one a crosslinked solid organopolysiloxane elastomer and at least one polymer which is soluble or swellable in water.

* * * * *

UNITED STATES PATENT AND TRADEMARK OFFICE
CERTIFICATE OF CORRECTION

PATENT NO. : 6,465,402 B1
DATED : October 15, 2002
INVENTOR(S) : Raluca Lorant

It is certified that error appears in the above-identified patent and that said Letters Patent is hereby corrected as shown below:

Title page,
Item [73], Assignee, "L'Oreal, Clinchy (FR)" should read -- L'Oreal, Clichy (FR) --.

Column 15,
Line 24, "

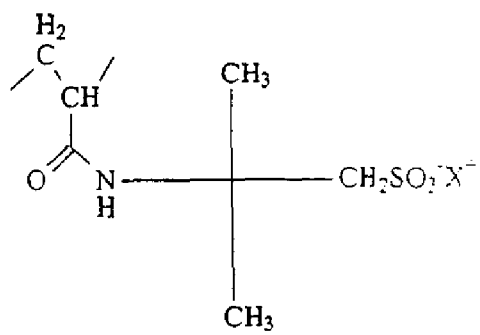

"

should read

-- 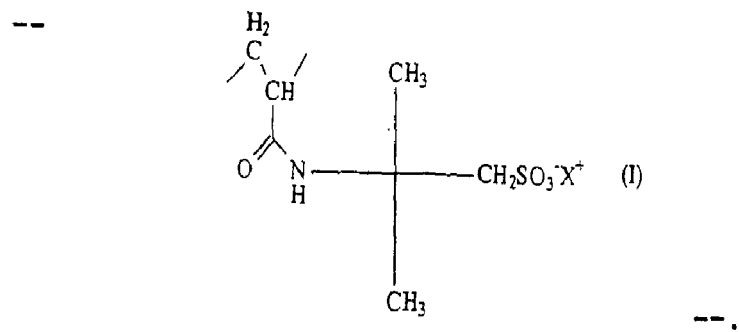 --.

UNITED STATES PATENT AND TRADEMARK OFFICE
CERTIFICATE OF CORRECTION

PATENT NO. : 6,465,402 B1  
DATED : October 15, 2002  
INVENTOR(S) : Raluca Lorant Page 2 of 2

It is certified that error appears in the above-identified patent and that said Letters Patent is hereby corrected as shown below:

Column 16,  
Line 5,

"

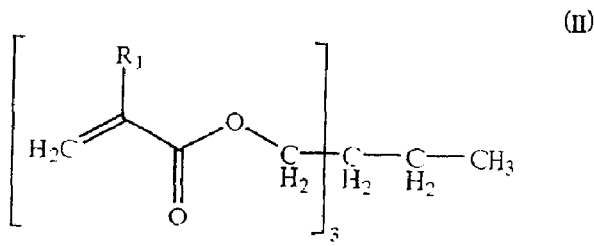

"

should read

--

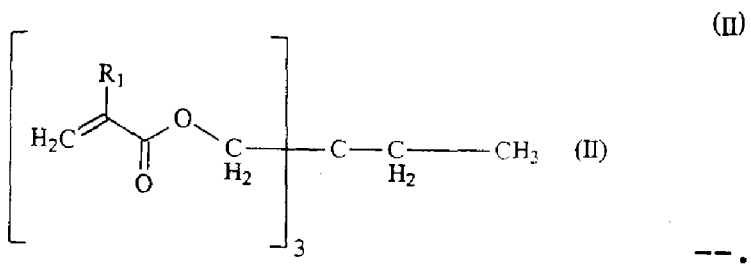

--.

Signed and Sealed this

Eighteenth Day of March, 2003

JAMES E. ROGAN  
*Director of the United States Patent and Trademark Office*